| United States Patent [19] | [11] | 4,148,830 |
|---|---|---|
| Pruett et al. | [45] | Apr. 10, 1979 |

[54] HYDROFORMYLATION OF OLEFINS

[75] Inventors: Roy L. Pruett, Charleston, W. Va.; James A. Smith, Cleveland Heights, Ohio

[73] Assignee: Union Carbide Corporation, New York, N.Y.

[21] Appl. No.: 683,534

[22] Filed: May 5, 1976

Related U.S. Application Data

[63] Continuation of Ser. No. 556,270, Mar. 7, 1975, abandoned, which is a continuation of Ser. No. 887,370, Dec. 22, 1969, abandoned.

[51] Int. Cl.$^2$ ............................................. C07C 45/10
[52] U.S. Cl. ............................................. 260/604 HF
[58] Field of Search ................. 260/604 HF, 632 HF; 568/909

[56] References Cited

U.S. PATENT DOCUMENTS

| 3,239,566 | 3/1966 | Slaugh et al. ................. 260/604 HF |
| 3,527,809 | 9/1970 | Pruett et al. ................. 260/604 HF |

FOREIGN PATENT DOCUMENTS

| 903589 | 8/1962 | United Kingdom ............ 260/604 HF |
| 1228201 | 4/1967 | United Kingdom ............ 260/604 HF |
| 1128934 | 10/1968 | United Kingdom ............ 260/604 HF |
| 1387657 | 3/1975 | United Kingdom ............ 260/604 HF |

*Primary Examiner*—Werren B. Lone
*Attorney, Agent, or Firm*—George A. Skoler

[57] ABSTRACT

A hydroformylation process whereby rhodium complex catalyst and excess triorganophorus ligand are employed, under mild conditions of temperature and pressure, to produce aldehydic products rich in the normal isomer thereof, the improvement representing the introduction and/or recycling of the rhodium complex in active form and soluble in a complex mixture of high boiling liquid condensation products rich in hydroxylic compounds.

10 Claims, No Drawings

HYDROFORMYLATION OF OLEFINS

This Application is a con't. of Ser. No. 556,270 filed Mar. 7, 1975, which is a con't. of Ser. No. 887,370 filed Dec. 22, 1976, both Abandoned.

This invention relates to an improvement in the Oxo process for preparing oxygenated products comprising aldehydes using rhodium in complex combination with carbon monoxide and triorgano phosphorus ligands as the catalyst therefor.

Processes directed to the production of reaction mixtures comprising substantial amounts of aldehydes and at times lesser amounts of alcohols by the reaction of olefinic compounds with carbon monoxide and hydrogen at elevated temperatures and pressures in the presence of certain catalysts are well-known in the art. The aldehydes and alcohols produced generally correspond to the compounds obtained by the addition of a carbonyl or carbinol group to an olefinically unsaturated carbon atom in the starting material with simultaneous saturation of the olefinic bond. Isomerization of the olefin bond may take place to varying degrees under certain conditions with the subsequent variation in the products obtained. Such processes are generally known in industry under varying names such as Oxo process or reaction, oxonation, and/or hydroformylation.

One disadvantage of prior art hydroformylation processes is their dependence upon the use of catalysts such as cobalt octacarbonyl which require exceptionally high operative pressures to maintain such catalysts in their stable form. Another disadvantage is the difficulty in obtaining hydroformylation products which have a relatively high normal to branched-chain isomer ratio.

In copending United States Application Ser. No. 658,055 entitled "Improved Hydroformylation Process" by R. L. Pruett and J. A. Smith, filed Aug. 3, 1967, there is disclosed a novel process for preparing oxygenated products comprising aldehydes which have high normal to iso- or branched-chain isomer ratios. Such process involves using certain rhodium complex compounds to effectively catalyze, in the presence of triorganophosphorus ligands, the Oxo reaction whereby olefinic compounds are reacted with hydrogen and carbon monoxide under a defined set of variables. Notably such variables include (1) the rhodium complex catalyst, (2) the olefinic feed, (3) the triorganophosphorus ligand and its concentration, (4) the relatively low temperature range, (5) the relatively low total gas pressure, and (6) the partial pressures exerted by hydrogen and carbon monoxide.

Among the catalysts which are contemplated in the process described in the aforesaid copending application include a wide variety of compounds which consist essentially of rhodium in complex combination with carbon monoxide and well-defined triorganophosphorus ligands as exemplified by triphenylphosphine. A typical active catalytic species is hydridoncarbonyltris(triphenylphosphine)rhodium(I) which has the formula $HRh(CO)(P\phi_3)_3$. The process is likewise effected in the presence of an excess of the triorganophosphorus ligand which can be considered, if desired, as a modifier or co-catalyst and/or diluent. By the practice of such process there is obtained, as indicated previously, an unexpectedly high normal/iso ratio of aldehydic products at commercially attractive reaction rates and efficiencies.

It is well known that rhodium (as an element or in compound form) is exceedingly expensive. Consequently, a successful commercial Oxo process based on rhodium complex catalysis must be extremely efficient. The operation of such process should not result in the loss of rhodium, or necessitate frequent regeneration of rhodium and/or rhodium-containing compounds to the suitable complex catalytic form.

Additionally, the expensive rhodium complex should remain dissolved in the reaction medium and thus be available to the reactants during the initial as well as the recycle contacts. Obviously, a commercial Oxo process based on rhodium complex catalysis would be subjected to severe inefficiencies and economic drawbacks, if not economic failure, should the rhodium-containing catalyst slowly disengage itself from solution as by precipitation, reduction to rhodium metal, etc.

A very real reason was present, therefore, to introduce the potential or active rhodium species into the Oxo reaction zone as a solution in an organic vehicle. The active catalyst, as is known in recent literature, can be preformed and then introduced into the reaction mixture media, or the active catalyst species can be prepared in situ during the hydroformylation reaction. As an example of the latter, (2,4-pentanedionato)dicarbonylrhodium(I) can be introduced into the reaction zone where, under the operative conditions therein, it reacts with the triorganophosphorus ligand, e.g., triphenylphosphine, to thus form active catalyst such as hydridocarbonyltris(triphenylphosphine)rhodium(I).

In the process set out in the aforesaid copending application, it is stated that the use of normally-liquid inert organic solvents may be desirable and practical in the practice of the described process. Illustrative of organic solvents would include toluene xylene, pyridine, tributylamine, 2-methyl-5-ethylpyridine, diethyl succinate, methyl isobutyl ketone, t-butanol, 1-butanol, ethyl benzoate, tetralin, acetonitrile, mixtures of benzonitrile and tetralin, and others. Though relatively high ratios of normal/iso isomers of aldehydic product were obtained in such hydroformylation reactions, eventually the product mixture at the termination of the reaction, either at room temperature or at the chosen operating temperature of, for example, 80° C., was either slightly cloudy in nature or noticeable precipitation had occurred. Elemental analyses indicate that such solids (cloudiness or precipitate) contain rhodium. In some instances it would appear that "polymeric" rhodium complex solids had formed; in other instances, the solids were similar to an active form of the rhodium complex species. Such solids could become lost in the system, deposit in small devices, plug valves, etc. Obviously, a truly and efficient commercial Oxo operation could not tolerate the loss of even small quantities of rhodium.

A further disadvantage of introducing the rhodium species as a solution in an extraneous organic liquid was the obvious requirement of separating the oxygenated product from such organic liquid. The initial introduction into the Oxo reaction zone of a catalytic solution in extraneous organic liquids is feasible. However, a truly commercially based Oxo operation demands continuous or intermittent catalyst introduction which can be fresh catalyst, regenerated catalyst, or catalyst contained in a recycle stream. Eventually, therefore, the separation or resolution of oxygenated product and extraneous organic liquid represents a disability which must be taken into account when calculating the over-all economics of the commercial process.

Thus, it was quite unexpected and unobvious indeed to discover that active rhodium complex compound could be introduced into the hydroformylation zone as a solution in a complex mixture of high boiling liquid condensation products. Moreover, not only did the hydroformylation reaction result in a high ratio of normal/iso isomer distribution of aldehydic product over extended period of times, but also the continuous recycling of the rhodium species in substantial quantities of such condensation products did not result in any noticeable precipitation of the rhodium in one form or another. In addition, no discernible loss in the life of the catalyst was detected over extended periods of operation. In addition, the use of such condensation products as the media to solubilize the rhodium-containing catalyst is advantageous from the standpoint that extraneous organic liquids can be excluded entirely from the hydroformylation zone, if desired. Since the instant novel process also contemplates, in preferred embodiments, the use of excess or free triorganophosphorus ligand in the reaction medium, it was rather surprising to also observe that the rhodium complex catalyst maintained its activity and solubility in a solution of such dissimilar liquids over long periods of continuous operation.

For sake of brevity and explanation purposes, let us consider the hydroformylation reaction of propylene to yield oxygenated products which contain a high normal/iso ratio of butyraldehydes. The operative conditions of such hydroformylation process are substantially similar to those described in the aforesaid copending application Ser. No. 658,055. That is to say, one is dealing with a relatively low pressure, rhodium complex catalyzed hydroformylation reaction that is quite efficient and, under the mild operative conditions employed, forms small quantities of by-products. However, the aldehydic products being reactive compounds themselves slowly undergo condensation reactions, even in the absence of catalysts and at comparatively low temperatures, to form high boiling liquid condensation products. Some aldehydic product, therefore, is involved in various reactions as depicted below using n-butyraldehyde as an illustration:

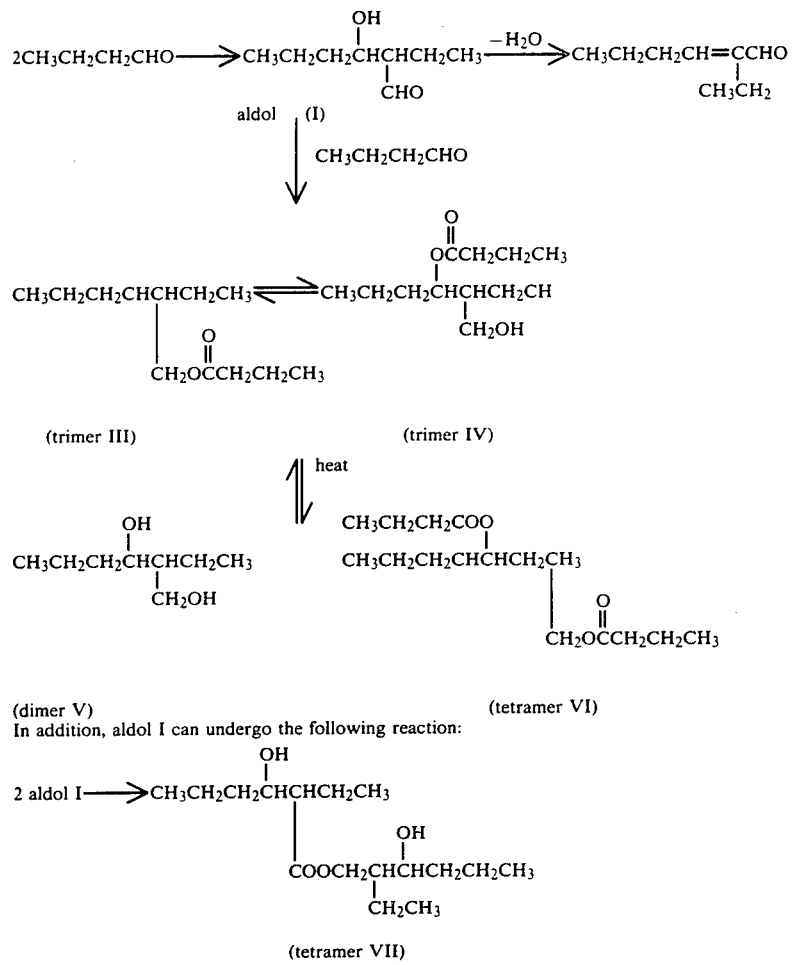

The names in parentheses in the afore-illustrated equations, aldol I, substituted acrolein II, trimer III, trimer IV, dimer V, tetramer VI, and tetramer VII, are for convenience only. Aldol I is formed by an aldol condensation; trimer III and tetramer VII are formed via Tischenko reactions; trimer IV by a transesterification reaction; dimer V and tetramer VI by a dismutation reaction. Principal condensation products are trimer III, trimer IV, and tetramer VII, with lesser amounts of the other products being present. Such condensation products, therefore, contain substantial quantities of hydroxylic compounds as witnessed, for example, by trimers III and IV and tetramer VII.

It is highly desirable to maintain the substituted acrolein II at low concentrations, e.g., below about 5 weight percent, since it has been observed that a build-up of this product tends to curtail the life of the rhodium complex catalyst. Resolution of the components comprising the high boiling liquid condensation products can be accomplished via conventional techniques.

Recent publications actually teach away or avoid mentioning the use of substantial quantities of hydroxylic compounds or carboxylic compounds as a solvent for Oxo catalysts comprised of rhodium in complex combination with carbon monoxide and triorgano phosphorus ligand. Thus, in Belgium Pat. No. 714,275, the following is stated:

The liquid media is preferably not a hydroxylic compound, e.g., an alcohol such as butanol, or a carboxylic compound such as propionic acid, since this class of compounds reacts with the aldehyde products or by-products of the reaction. It is preferred that the solvent contain no more than 5 percent by weight, or more preferably no more than 2 percent by weight of hydroxylic compounds.

In U.S. Pat. No. 3,239,566 issued Mar. 8, 1966, the patentees in discussing the use of solvents state the following:

However, the use of solvents which are inert, or which do not interfere to any substantial degree with the desired hydroformylation reaction under the conditions employed, may be used within the scope of the invention. Saturated liquid hydrocarbons, for example, may be used as solvent in the process, as well as ketones, ethers, and the like.

In a preferred embodiment, the invention resides in the discovery that the expensive rhodium complex species can be introduced into the hydroformylation zone as a catalytically active solution in high boiling liquid condensation products with/without triorganophosphorus ligand. These high boiling liquid condensation products result from the condensation reactions of $C_3$ to $C_{20}$ alkanals, preferably $C_3$ to $C_{10}$ alkanals. Such reactions include the aldol condensation, Tischenko, transesterification, and/or dismutation reactions illustrated previously. The high boiling liquid condensation products thus represent a complex mixture containing significant quantities of the appropriate trimer III, trimer IV, and/or tetramer VII as well as lesser amounts of the appropriate aldol I, substituted acrolein II, dimer V, and/or tetramer VI. As indicated previously, it's highly desirable that substituted acrolein II be kept at low concentrations. The resolution of various components in this complex mixture of condensation products can be effected via well-known techniques. Thus, various minor components can be removed from the mixture if so desired.

The high boiling liquid condensation products can be preformed and then used as a solvent medium for introducing the rhodium species into the hydroformylation zone. High boiling liquid condensation products also can be recovered from the stripping operation as residue products which can be used as the solvent medium for so carrying the rhodium species into the hydroformylation zone.

In general, it oftentimes may be desirable to employ a solution of high boiling liquid condensation products and triorganophosphorus ligand as the solvent medium for the rhodium species. Such solutions can contain significant quantities of the triorganophosphorus ligand, e.g., up to about 35 weight percent and higher if so desired. In certain instances, it may also be desirable to use minor amounts of an organic cosolvent which is normally-liquid and inert during the hydroformylation process, e.g., toluene, cyclohexanone, etc.

In another preferred embodiment, we have discovered that a solution of the rhodium species in high boiling liquid condensation products with/without triorganophosphorus ligand with/without aldehydic product(s) (resulting from the hydroformylation reaction) can be recovered from the hydroformylation system and continuously or intermittently recycled to the hydroformylation zone over extraordinarily long periods of time without any detectable loss of rhodium, catalyst life, reaction rates, and efficiencies. This is truly a significant discovery since a commercial Oxo process based on rhodium complex catalysis must be extremely efficient, and it must result in practically no loss in rhodium values while maintaining maximum catalyst activity and solubility.

This recycle feature may be effected continuously or intermittently. At times it may be desirable to bleed off a portion of the recycle stream to regenerate the rhodium catalyst, to prevent an extraordinarily build-up of the high boiling liquid condensation products, etc. It may also be desirable to add fresh rhodium catalyst either to the recycle stream or separately to the hydroformylation reaction zone. The temperature of the recycle stream does not appear to be critical and it may vary from about 20° C. to the maximum Oxo temperature contemplated, and higher. It is desirable that the recycle stream be a solution of the condensation products triorganophosphorus ligand, and aldehydic products. In this respect, the recycle stream can tolerate large quantities of such ligand and aldehydic products, e.g., a major portion by weight of the recycle stream may comprise triorganophosphorus ligand plus aldehydic products.

Initially, the hydroformylation reaction can be effected in the absence or in the presence of small amounts of high boiling liquid condensation products as a solvent for the rhodium complex, or the reaction can be conducted with upwards to about 70 weight percent, and even as much as about 90 weight percent, and more, of such condensation products, based on the total liquid medium. We feel that this discovery advances the rhodium catalyzed Oxo process to the commercially practicable range since the expensive rhodium complex catalyst is maintained in active and dissolved form (in such condensation products), and it is available to the reactants during the initial as well as recycle contacts.

By the term "high boiling liquid condensation products" as used herein is meant the complex mixture of high boiling liquid products which result from the condensation ractions of the $C_3$ to $C_{21}$ alkanal, preferably $C_4$ to $C_{10}$ alkanal, as illustrated previously in the series of equations involving n-butyraldehyde as the model. Also, as indicated previously, such condensation products can be preformed or produced in situ in the Oxo process. It is these relatively high boiling liquid condensation products in which the rhodium complex species is soluble therein while exhibiting high catalyst life over extended periods of continuous hydroformylation. Of the components comprising the high boiling liquid condensation products, the hydroxylic compounds designated as trimer III, trimer IV, and tetramer VII represent the principal species.

The hydroformylatin process involves contacting (1) an alpha-olefin of 2 to 20 carbon atoms, preferably from 2 to 10 carbon atoms; (2) with carbon monoxide and hydrogen; (3) in the presence of a catalytic quantity of a complex catalyst consisting essentially of rhodium in complex combination with carbon monoxide and a triorganophosphorus ligand, each organo moiety being monovalently bonded to the phosphorus atom through a carbon atom or an aliphatic etheric oxygen atom, said phosphorus atom possessing one available pair of electrons, said triorganophosphorus ligand having a ΔHNP value of at least about 425; (4) in the presence of high boiling liquid condensation products as a solvent for said catalyst; (5) at least 2 mols of free triorgano phosphorus compound as defined above per mol of rhodium; (6) at a temperature in the range of from about 50° C. to 145° C.; (7) at a total pressure of carbon monoxide and hydrogen of less than about 450 psia; and (8) a partial pressure attributable to carbon monoxide no greater than about 75 percent of said total pressure; (9) thereby reacting said alpha olefinic compound with said carbon monoxide and hydrogen with the formation of oxygenated products rich in normal aldehydes which have one more carbon atom than said alpha olefinic compound.

It is essential that the aforesaid triorganophosphorus ligands possess a ΔHNP value of at least about 425, and preferably at least about 500. By "ΔHNP" is meant the difference in the half-neutralization potential between the ligand under consideration and N,N'-diphenylguanidine as determined according to the procedure set out in the article by C. A. Streuli, Analytical Chemistry, 32, 985-987 (1960). The ΔHNP value is a measure of the basicity of the ligand. For example, the relatively strong basic phosphorus-containing ligands such as those possessing a ΔHNP value substantially below 425 gave complexes that were inffective in the practice of the invention as evidenced by a lack of a discernible reaction rate and/or low normal to branched-chained aldehydic product isomer ratios. Those phosphorus-containing ligands which possessed a ΔHNP value of at leat about 425, and preferably at least about 500, are relatively less basic compounds. Complex catalysts prepared from such ligands effectively catalyzed the novel process whereby there resulted in a product mixture which contained a high normal to branched-chained aldehydic isomer ratio.

In Table A below, the ΔHNP values of several illustrative phosphorus-containing ligands are set out.

TABLE A

| LIGAND | ΔHNP[1] |
|---|---|
| $P(CH_3)_3$ | 114 |
| $P(C_2H_5)_3$ | 111 |
| $P(n-C_3H_7)_3$ | 115 |
| $P(n-C_4H_9)_3$ | 131 |
| $P(iso-C_4H_9)_3$ | 167 |
| $P(n-C_5H_9)_3$ | 139 |
| $P(2-n-C_4H_9OC_2H_4)_3$ | 162 |
| $P(2-C_6H_5C_2H_4)_3$ | 273 |
| $P(C_6H_{11})_3$ | 33 |
| $P(CH_3)(C_2H_5)_2$ | 117 |
| $P(CH_3)_2(C_2H_5)$ | 117 |
| $P(CH_3)_2(C_6H_5)$ | 281 |
| $P(C_2H_5)_2(C_6H_5)$ | 300 |
| $P(C_6H_{11})_2(2-CNC_2H_4)$ | 232 |
| $P(CH_3)_2(2-CNC_2H_4)$ | 291 |
| $P(n-C_4H_9)_2(2-CNC_2H_4)$ | 282 |
| $P(n-C_8H_{17})_2(2-CNC_2H_4)$ | 297 |
| $P(p-CH_3OC_6H_4)_3$ | 439 |
| $P(C_6H_5)_3$ | 573 |
| $P(C_6H_5)_2(C_2H_5)$ | 400 |
| $P(C_6H_5)_2(n-C_4H_9)$ | 400 |
| $P(O-n-C_4H_9)_3$ | 520 |
| $P(OCH_3)_3$ | 520 |
| $P(OC_6H_5)_3$ | 875 |

[1] E. M. Thorsteinson and F. Basolo.
J.Am. Chem. Soc. 88, 3929-3936 (1966)
C. A. Streuli, Analytical Chemistry, 32, 985-987 (1960)

By way of illustrations, suitable classes of triorgano-containing ligands which are contemplated in the practice of the invention include the trialkylphosphites, the triarylphosphites, and the triarylphosphines. Desirably each organo moiety in the ligand does not exceed 18 carbon atoms. The triarylphosphines represent the preferred class of ligands. Specific examples of ligands which are suitable in forming the complex catalysts includetrimethylphosphite, tri-n-butylphosphite, tri-phenylphosphite, trinaphthylphosphite, triphenylphosphine, trinaphthylphosphine, phenyl diphenylphosphinite, diphenyl phenylphosphonite, diphenyl tris (p-chlorophenyl)phosphine, tri(p-methoxyphenyl)phosphite, and the like. Triphenylphosphine is the most preferred ligand since it resulted in complex catalysts which effectively catalyzed alpha olefinic compounds at highly satisfactory reaction rates and also yielded high normal-to branched-chain aldehydic product isomer ratios.

As indicated previously, the trivalent phosphorus-containing ligand should have a ΔHNP value of at least about 425. Moreover, these ligands should be free of interfering or so-called sterically hindered groups. Ligands such as the triarylphosphines and the triarylphosphites which are characterized by the presence of "bulky" groups, e.g., phenyl, tolyl, etc., in the ortho position of the aryl moieties have been observed to give catalyst complexes which are unsuitable in the practice of the invention.

The novel process contemplates alpha olefins of 2 to 20 carbon atoms, preferably 2 to 10 carbon atoms, as reactants in the novel process. Such alpha olefin are characterized by a terminal ethylenic carbon-to-carbon bond which may be a vinylidene group, i.e., $CH_2=C-$, or a vinyl group, i.e., $CH=CH-$. They may be straight-chain or branched-chain and may contain groups or substituents which do not essentially interfere with the course of the novel process. Illustrative alpha olefinic compounds which can be employed as reactants include ethylene, propylene, 1-butene, 2-methyl-1-butene, 1-pentene, 1-hexene, 1-heptene, 1-octene, 2-ethyl-1-hexene, 1-dodecene, 1-octadecene, and the like.

The novel process is effected in the presence of a catalytically significant quantity of the complex catalyst. The hydroformylation reaction will proceed when employing as little as about $1 \times 10^{-6}$ mol, and even lesser amounts, of rhodium (from the complex catalyst) per mol of alpha olefinic feed. However, such catalyst concentrations, though operable, are not particularly desirable since the reaction rate appears to be too slow and thus not commercially attractive. The upper catalyst concentration limit can be as high as about $1 \times 10^{-1}$ mol, and higher, of rhodium per mol of alpha olefinic feed. However, the upper limit appears to be dictated and controlled more by economics in view of the high cost of rhodium metal and rhodium compounds. No particular advantages at such relatively high concentrations are manifest. A catalyst concentration of from about $1 \times 10^{-5}$ mol to about $5 \times 10^{-2}$ mol of rhodium metal per mol of alpha olefinic feed is desirable. A concentration of from about $1 \times 10^{-4}$ to about $1 \times 10^{-2}$ mol of rhodium per mol of alpha olefin is preferred. Our observations generally indicate that optimum results are obtained by employing a catalyst concentration falling within the aforedefined preferred range. It is thus apparent that the concentration of the complex catalyst can vary over a rather wide range.

Regardless whether one preforms the active complex catalyst prior to introduction in the hydroformylation reaction zone or whether the active catalyst species is prepared in situ during the hydroformylation reaction, it is essential that the reaction be effected in the presence of free ligand. By "free ligand" is meant the triorganophosphorus compounds as exemplified by triphenylphosphine that are not tied to or complexed with the rhodium atom in the active complex catalyst. Though we do not wish to be held to any theory or mechanistic discourse, it appears that one active catalyst species contains, in its simplest form, a concentration of triorgano phosphorus ligand and carbon monoxide equal to a total of four mols in complex combination with one mol of rhodium. As can be surmised from the above discussion, carbon monoxide (which incidently is also properly classified as a ligand) is likewise present and complexed with the rhodium in the active species. In some instances, the active catalyst species can also contain hydrogen as a ligand.

In a desirable embodiment, the novel process is effected by employing a hydroformylation reaction mixture which contains at least about 2 mols of free triorganophosphorus ligand per mol of rhodium. It is preferred that at least about 10 mol of free triorganophosphorus ligand per mol of rhodium be employed. The upper limit does not appear to be critical and its concentration would be dictated largely by commercial and economic considerations. The use of large quantities of ligand serves to function as a codiluent with the hydroxylic-containing condensation products.

A unique feature of the invention is the exceptionally low total pressures of hydrogen and carbon monoxide which are required to effect a commercial process. Total pressures of hydrogen and carbon monoxide less than about 450 psia and as low as one atmosphere, and lower, can be employed with effective results. Total pressures of less than about 350 psia are preferred.

The partial pressure of the carbon monoxide has been found to be an important factor in the novel process. It has been observed that a noticeable decrease occurs in the normal/iso aldehydic product isomer ratio as the partial pressure attributable to carbon monoxide approaches a value of about 75 percent of the total gas pressure (CO + H$_2$). However, in certain instances it may be plausible to increase the carbon monoxide partial pressure to a value of above about 75 percent of the total gas pressure. In general, a partial pressure attributable to hydrogen of from about 25 to about 95 percent and more, based on the total gas pressure (CO + H$_2$) is suitable. It is generally advantageous to employ a total gas pressure in which the partial pressure attributable to hydrogen is greater than the partial pressure attributable to carbon monoxide, e.g., the hydrogen to carbon monoxide ratio being between 3:2 and 20:1.

Another important variable of the novel process is the exceptionally low operative temperatures which can be employed in conjunction with the extremely low operative pressures and other well-defined variables. Our novel process can be conducted at temperatures as low as about 50° C. and up to 145° C. with advantageous results. A temperature in the range of from about 60° C. to about 130° C. is preferred.

The concentration of the alpha olefinic feed can vary over an extremely wide range. For example, one could employ ratios of alpha olefinic feed to complex catalyst between about 1200:1 and about 1:8. However, it must be understood that such ratios are merely illustrative and higher as well as lower ratios are contemplated and are within the scope of the invention.

The residence period can vary from about a couple of minutes to several hours in duration and, as is well appreciated, this variable will be influenced, to a certain extent, by the reaction temperature, the choice of the alpha olefinic reactant, of the catalyst, and of the ligand, the concentration of the ligand, the total synthesis gas pressure and the partial pressure exerted by its components, and other factors. As a practical matter the reaction is effected for a period of time which is sufficient to hydroformylate the alpha or terminal ethylenic bond of the alpha olefinic reactant.

The preparation of the catalysts employed in the novel hydroformylation reaction is documented in the literature. A suitable method is to combine the rhodium salt of an organic acid with the ligand, e.g., triphenylphosphite, triphenylphosphine, etc., in liquid phase. The valence state of rhodium may then be reduced by hydrogenating the solution prior to the use of the catalysts therein. Alternatively, the catalysts may be prepared from a carbon monoxide complex of rhodium. For example, one could start with dirhodium octacarbonyl, and by heating this substance with the ligand, the ligand will replace one or more of the carbon monoxide molecules, thus producing the desired catalyst. It is also possible to start with the ligand of choice and rhodium metal; or an oxide of rhodium, and prepare the active catalyst species in situ during the hydroformylation reaction.

The hydroformylation process can be conducted in continuous, semi-continuous, or batch fashion. If desired, the catalyst can be added to hydroformylation zone batchwise, continuous, and/or incrementally. Aldehydic products can be recovered from the hydroformylation reaction product mixture, for example, by first cooling the effluent from the hydroformylation zone, the passing same through a let-down valve in which the pressure is substantially reduced, e.g., atmospheric pressure. Thereafter, the effluent can be passed through a first long-tube vaporizer to flash off hydrogen, carbon monoxide, unreacted alpha-olefinic reactant, etc., at ambient temperature, and then introduced into a second long-tube, which can be maintained at elevated temperatures, e.g., about 100° C. or less to about 160° C. and higher, at about 1 mm. of Hg to 760 mm. of Hg (the operative conditions primarily depending upon the nature of the aldehydic products) to thus strip or recover the aldehydes as an overhead fraction. The liquid residue fraction comprises some unrecovered aldehydic product, free triorganophosphorus ligand, some high boiling condensation products, and rhodium values.

The following Examples have been set out merely to illustrate the process of the invention.

In Examples 1 through 10 below, the pressure vessels employed was either 200 milliliters or 775 milliliters in capacity. These vessels were heated using oil baths and agitated by means of magnetic stirrers. The following is a typical procedure: measured quantities of solvent, octene-1, triorganophosphorus ligand, and rhodium complex are charged to the reaction vessel. The reactor is sealed, flushed with carbon dioxide, then heated (about 80° C.) with stirring. At this temperature, the vessel is pressured alternately with 10 psig carbon monoxide and then 10 psig hydrogen until 30 psi of each gas has been added. The pressure is maintained between 60–70 psig during the reaction by addition of 5 psig each of carbon monoxide and hydrogen whenever the pressure drops to 60 psig. The reaction time is about 60 minutes and the total pressue drop is 110 psig. After cooling the vessel to room temperature and venting, the reaction product mixture are analyzed directly by gas liquid partition chromatography. Pertinent data are set out in Table I below:

TABLE I

| Example | Solvent; Ml. | Ratio of Normal To 150 Co Aldehyde | Appearance Of Reaction Mixture | | |
|---|---|---|---|---|---|
| | | | Beginning Of Reaction | During Reaction; 80° C. | End Of Reaction; 22° C. |
| 1. | Xylene; 150 ml.[a] | 8.3 | Clear | Clear | Slightly Cloudy |
| 2. | Tributylamine; 150 ml.[a] | 4.7 | Complex | Never Totally Soluble | |
| 3. | Ethyl Benzoate; 150 ml.[a] | 9.7 | Clear | Slightly Cloudy | Slightly Cloudy |
| 4. | 2-Methyl-5-Ethylpyridine;[a] 150 ml. | 5.3 | Cloudy | Cloudy | Precipitate |
| 5. | Diethyl Succinate; 40 ml.[b] | 8.4 | Cloudy | Cloudy | Very Cloudy |
| 6. | Methyl i-Butyl Ketone; 40 ml.[b] | 10.0 | Cloudy | Cloudy | Very Cloudy |
| 7. | Acetonitrile; 40 ml.[b] | 12.0 | Cloudy | Cloudy | Cloudy |
| 8. | t-Butanol; 40 ml.[c] | 6.1 | Cloudy | Cloudy | Precipitate |
| 9. | n-Butanol; 40 ml.[c] | 7.0 | Cloudy | Clear | Precipitate |
| 10. | N,N'-Dimethylaniline;[c] 40 ml. | 4.7 | Cloudy | Amost Clear | Slightly Cloudy |

[a]Hydroformylation of 15 grams of octene-1 using 0.4 gram HRh(CO) (P$\phi_3$)$_3$ and 3.0 gram of P(O$\phi_3$.
[b]Hydroformylation of 3.6 grams of octene-1 using 0.1 gram HRh(CO) (P$\phi^3$)$_3$ and 0.95 gram of P(O$\phi$)$_3$.
[c]Hydroformylation of 3.6 grams of octene-1 using 0.1 gram HRh(CO) (P$\phi_3$)$_3$ and 1.0 gram of P$\phi_3$.

EXAMPLE 11

A solution of 174 g. of n-tridecanal, 34 g. of triphenylphosphine and 0.27 g. of HRh(CO)(PPh$_3$)$_3$ was heated at 130° C., under a nitrogen atmosphere, for 65 hours. Analysis at the end of this time showed that 50 g. of n-tridecanal had reacted to form high boiling liquid condensation products.

The above solution was charged into a 3-liter autoclave. One mole of octene-1 was added, the autoclave was then sealed and pressurized with 50 psig each of carbon monoxide and hydrogen. Rocking of the autoclave was begun and it was heated to 80° C. The temperature was maintained at 80°-82° C. and the pressure at 100-120 psig by periodic addition of 1:1 H$_2$:CO gas mixture. After a period of 110 minutes gas absorption ceased and the vessel and contents were cooled and the excess gases were vented. Vapor phase chromatography analysis of the product indicated that n-nonanal and alphamethyloctanal were formed in the ratio 7.3:1.

EXAMPLE 12

High boiling liquid condensation products were prepared by heating n-butyraldehyde at 100°-110° C. for two weeks. Unreacted n-butyraldehyde was removed by flash distillation at reduced pressure. The high boiling liquid condensation products contained about 80 weight percent of trimer III, trimer IV, and tetramer VII; about 20 weight percent of aldol I and substituted acrolein II; and very small amounts of tetramer V and tetramer VI.

A solution was prepared which analyzed 8.2 weight percent cyclohexanone, 74.6 weight percent high boiling liquid condensation products, 16.5 weight percent triphenylphosphine ligand, and 488 parts per million rhodium (analyzed as the metal but present as HRh(CO)(P$\phi_3$)$_3$). This solution was fed into a continuous reactor, 2-liter size, at the rate of 1240 gms/hr. Propylene was fed into the reactor at the rate of 129 gms/hr. The temperature was maintained at 97° C. and the partial pressure of hydrogen was 194 psig and of carbon monoxide was 20.4 psig. The effluent from the reactor contained n-butyraldehyde and isobutyraldehyde in a 9.1/1 ratio.

EXAMPLE 13

A 7.2 liter stirred reactor was fed continuously with the following:

Hydrogen: 20.5 cubic feet/hour
Carbon Monoxide: 10.5 cubic feet/hour
Propylene: 2.1 pounds/hour
Catalyst Solution: 3000 cc/hour The catalyst solution represents the recycled stream and contains 490 parts per million rhodium calculated as the metal (in the form, however, HRh(CO)(P$\phi_3$)$_3$); 6.2 weight butyraldehyde products not removed during the stripping operation; 12.4 weight percent triphenylphosphine; and high boiling liquid condensation products consisting predominantly of trimer III, trimer IV, and tetramer VII, and lesser amounts of dimer V and tetramer VI.

The reactor and contents were maintained at 110° C. by means of an internal coil fitted with steam and cooling water. The total pressure was 82 psig, the partial pressures being as follows: pCO=10 psia; pH$_2$=37 psia; and pC$_3$H$_6$=37 psia.

The effluent from the reactor was cooled and then passed through a let-down valve in which the pressure was reduced to atmospheric. The liquid reaction product mixture was then passed through a stainless steel long-tube vaporizer to flash off excess H$_2$, CO, and C$_3$H$_6$ at ambient temperature. Thereafter, the liquid reaction product mixture was passed through another long tube vaporizer, maintained at about 130° C. This served to remove overhead the bulk of the normal- and iso-butyraldehydes which were produced at a rate of 1000 cc/hour. The ratio of normal- to iso-butyraldehyde was 0.5:1. The liquid solution recovered from the bottom of the vaporizer is the catalyst solution mentioned above and is recycled to the reactor at the stated rate.

This experiment was continued uninterrupted for 720 hours with no detectable loss of rhodium or of catalyst activity.

EXAMPLE 14

For the hydroformylation of 1-nonene, the 1-nonene is introduced into the reactor at the rate of 6.2 pounds/hour. The feed rates of hydrogen, carbon monoxide, and catalyst solution as well as the partial pressures of carbon monoxide and hydrogen and the hydroformylation were essentially the same as in Example 13 above. The second long tube vaporizer is maintained, however, at about 130° C. under a pressure of about 2mm. of Hg. in order to vaporize the normal- and isodecaldehyde products. The ratio of n-decaldehyde to isodecaldehyde is approximately 7:1. The recycle solution, i.e., catalyst solution, contains about 10 weight percent decanals; about 12 weight percent triphenylphosphine; and high boiling liquid condensation products consisting predominantly of trimer III, trimer IV, and tetramer VII, and lesser amounts of dimer II and tetramer VI.

After 250 hours of uninterrupted operation, no loss of rhodium or catalyst life is detected.

What is claimed is:

1. In the process of hydroformylating alphaolefins of 2 to 20 carbon atoms to form aldehydes comprising feeding of such alpha-olefin, hydrogen and carbon monoxide to a liquid homogeneous medium at a temperature between about 50° C. and 145° C. which medium contains (i) a solvent therein, (ii) a catalytic amount of rhodium in complex combination with carbon monoxide and triphenylphosphine, (iii) an additional amount of triphenylphosphine such that there is present at least two moles of free triphenylphosphine per mole of rhodium in said medium and (iv) products of the hydroformylation reaction; the total pressure of carbon monoxide and hydrogen is less than 450 psia with a partial pressure attributable to carbon monoxide of no greater than about 75 percent of the total pressure; all of which is sufficient to produce said aldehydes, and recovering aldehydes from said medium; wherein the improvement comprises employing higher boiling aldehyde condensation products containing hydroxyl groups as the solvent in said medium.

2. The process of claim 1 wherein at least a portion of said medium is removed prior to separation of said aldehydes and after removal of aldehydes from said medium, the medium is recycled to the hydroformylation reaction.

3. The process of claim 2 wherein the alphaolefin is propylene.

4. The process of claim 1 wherein there is present in the liquid medium less than about 5 percent by weight of substituted acrolein by-product.

5. The process of claim 3 wherein there is present in the liquid medium less than about 5 percent by weight of substituted acrolein by-product.

6. The process of claim 2 wherein the alphaolefin is 1-octene or 1-nonene.

7. The process of claim 6 wherein the alphaolefin is 1-octene.

8. The process of claim 2 wherein the alphaolefin is 1-octadecene.

9. The process of claim 1 wherein the rhodium is dissolved in a solution containing the high boiling liquid condensation product containing hydroxyl groups prior to providing it in the liquid homogeneous medium.

10. The process of claim 9 wherein the rhodium is first dissolved in a mixture comprising the high boiling liquid condensation product and triphenylphosphine.

* * * * *

UNITED STATES PATENT AND TRADEMARK OFFICE
CERTIFICATE OF CORRECTION

PATENT NO. : 4,148,830
DATED : April 10, 1979
INVENTOR(S) : Roy L. Pruett and James A. Smith It is certified that error appears in the above-identified patent and that said Letters Patent are hereby corrected as shown below:

Col. 1, line 6, "1976" should be --1969--.

Col. 4, line 13 under the product formula "$CH_3CH_2CH_2CH=\underset{\underset{CH_3CH_2}{|}}{C}CHO$" insert the designation ---substituted acrolein (II)---.

Col. 12, line 55, the ratio "0.5:1" should be ---10.5:1---.

Signed and Sealed this

*Twenty-fifth* Day of *December 1979*

[SEAL]

*Attest:*

SIDNEY A. DIAMOND

*Attesting Officer*   *Commissioner of Patents and Trademarks*